United States Patent [19]

Vannier et al.

[11] Patent Number: 5,082,001
[45] Date of Patent: Jan. 21, 1992

[54] ENHANCED COMPUTER BASED UPPER EXTREMITY EVALUATION SYSTEM

[76] Inventors: Michael W. Vannier, 709 Riverview Dr., Alton, Ill. 62002; Paul G. Groszewski, 5622 Delmar Apt. 604, St. Louis, Mo. 63112; Pamela J. Grasse, 7053 Pershing Ave., St. Louis, Mo. 63130

[21] Appl. No.: 520,527

[22] Filed: May 8, 1990

Related U.S. Application Data

[63] Continuation-in-part of Ser. No. 314,188, Feb. 27, 1989, Pat. No. 4,922,925.

[51] Int. Cl.$^5$ .............................................. A61B 5/103
[52] U.S. Cl. .................................................... 128/774
[58] Field of Search ............... 128/774, 779, 781, 782; 340/324 R; 364/963.1

[56] References Cited

U.S. PATENT DOCUMENTS

| | | | |
|---|---|---|---|
| 3,292,489 | 12/1966 | Johnson et al. | 364/963.1 |
| 3,651,509 | 3/1972 | Ngo | 340/324 R |
| 4,571,834 | 2/1986 | Fraser et al. | 128/782 |
| 4,649,934 | 3/1987 | Fraser et al. | 128/774 |
| 4,760,851 | 8/1988 | Fraser et al. | 128/774 |
| 4,885,687 | 12/1989 | Carey | 128/774 |

Primary Examiner—Max Hindenburg
Attorney, Agent, or Firm—Rogers, Howell & Haferkamp

[57] ABSTRACT

An enhanced upper extremity evaluation system includes a computer and a directly connected three-dimensional position locator including a wand which may be used by a therapist to enter data by positioning the wand on a desk top template instead of by typing a keyboard. Also, the three-dimensional position locator may be used in an "increment" mode to trace contours, scars or the like, and make other anthropometric measurements.

7 Claims, 5 Drawing Sheets

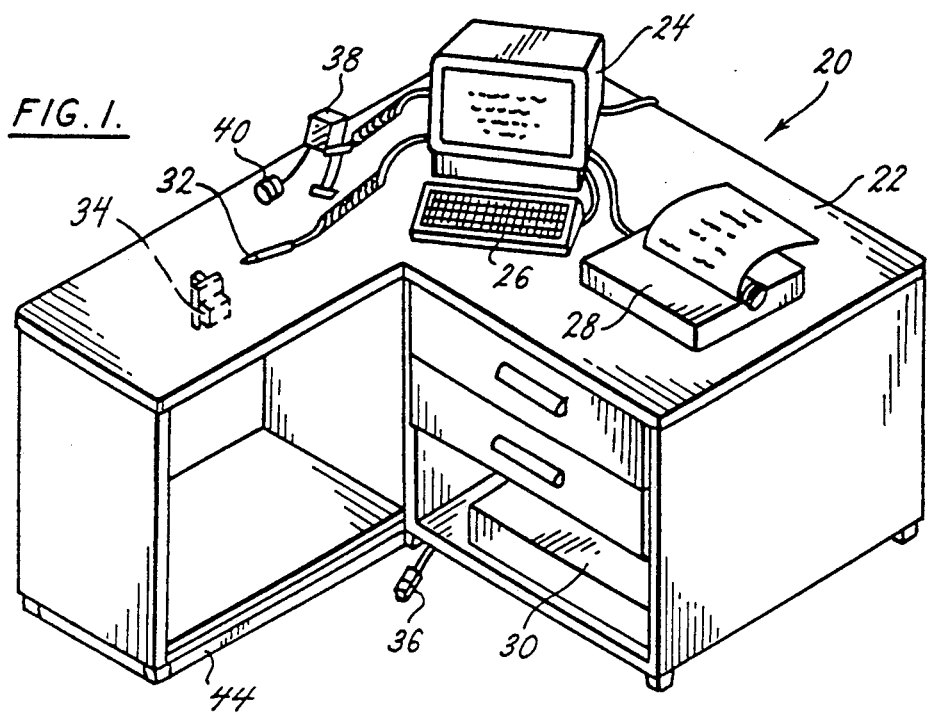
FIG. 1.
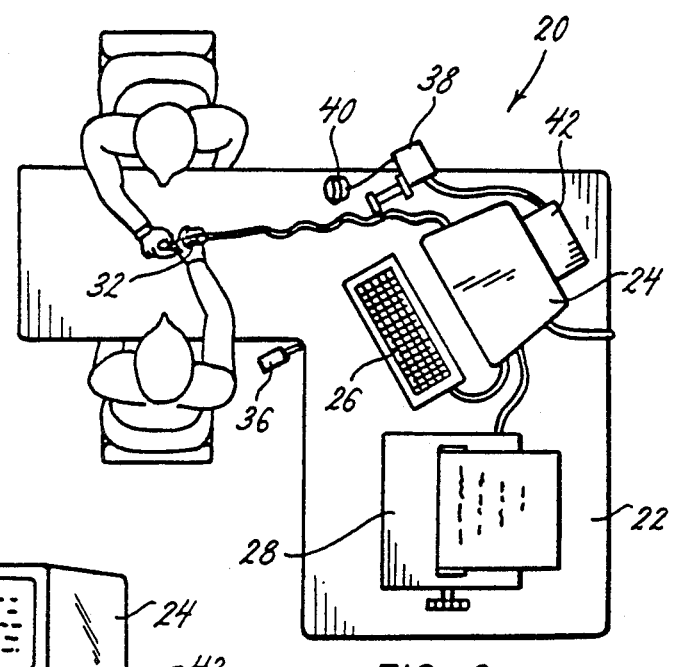
FIG. 2.
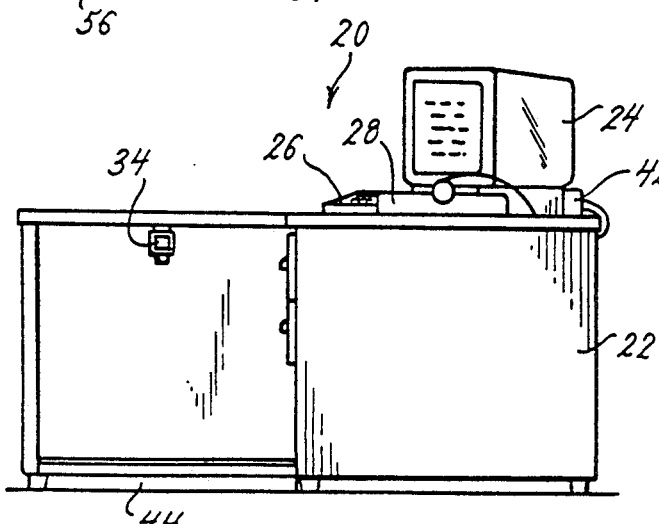
FIG. 4.
FIG. 3.

FIG. 5.

SAVE  PRINT  HELP  IMPORT

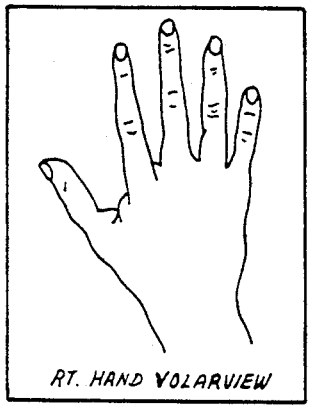
RT. HAND VOLAR VIEW

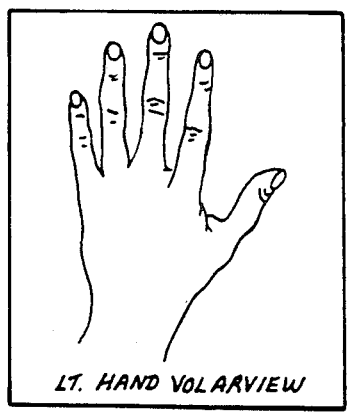
LT. HAND VOLAR VIEW

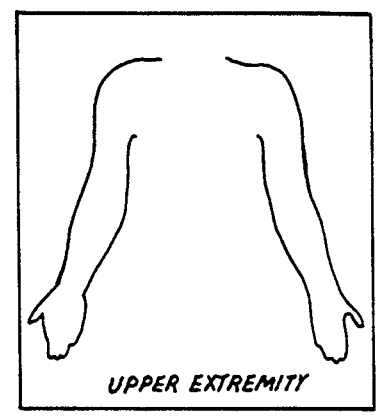
UPPER EXTREMITY

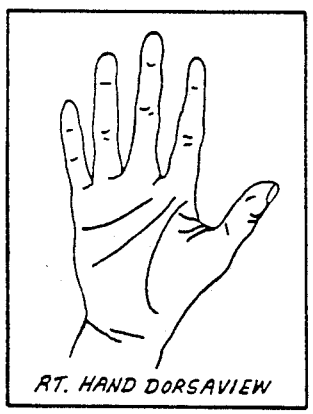
RT. HAND DORSAVIEW

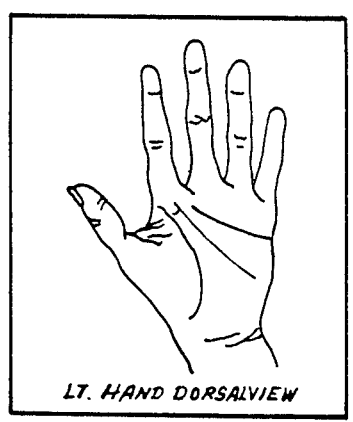
LT. HAND DORSAL VIEW

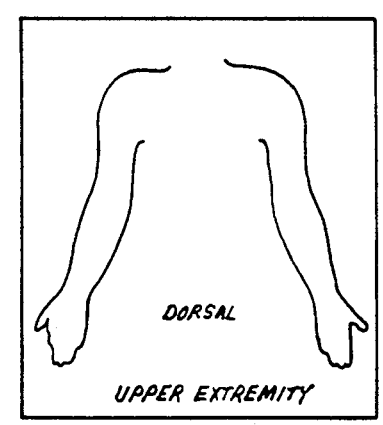
DORSAL
UPPER EXTREMITY

| COVER PAGE | ROM | PVD | SUMMARY |
| PERTINENT HISTORY | LATERAL | PNS | OTHER |
| COMPLAINTS | DORSAL | STRENGTH | OTHER |
| GRIP STRENGTH | RAPID LATERAL | PAM/DR. | OTHER |
| PINCH STRENGTH | SCAR | DIGIT IMPAIR | OTHER |
| AMPUTATION | SENSATION | JOINT IMPAIR | OTHER |
| ARTHRODESIS | ARTHROPLASTY | PERM. SKIN IMPAIR. | OTHER |

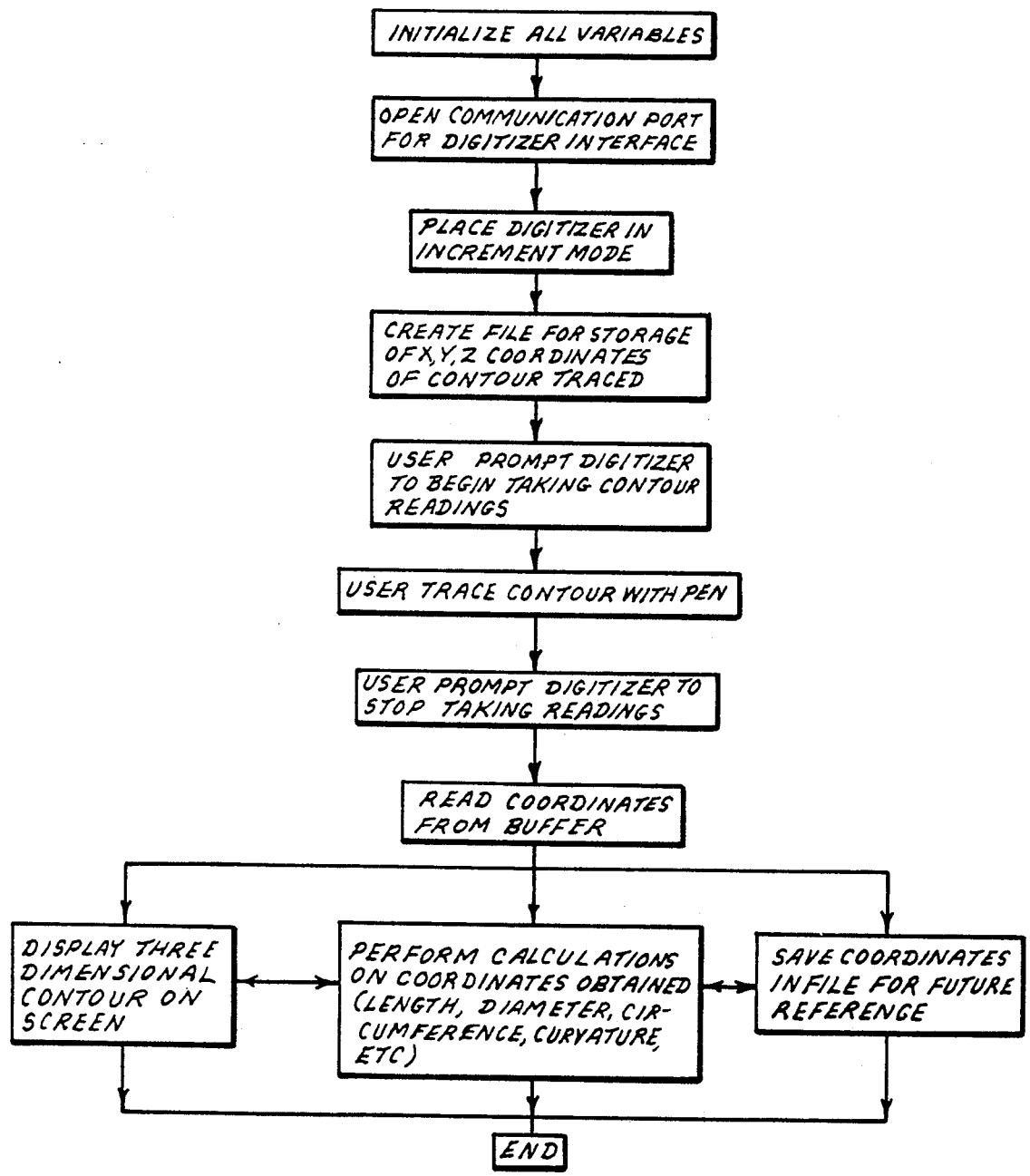

ENHANCED COMPUTER BASED UPPER EXTREMITY EVALUATION SYSTEM

CROSS REFERENCE TO RELATED APPLICATION

This application is a continuation-in-part of U S. patent application Ser. No. 07/314,188 filed Feb. 27, 1989, now U.S. Pat. No. 4,922,925.

BACKGROUND AND SUMMARY OF THE INVENTION

Clinical evaluation of a patient's upper extremities, and more particularly the hands, for disability can be a time-consuming process for skilled therapists and physicians. Because of the unique complexity of the hands' movements, multiple measurements must be taken across all joints of the fingers to determine their maximum angle of flexion and extension. There are fourteen joints or knuckles in a normal hand, and each of these must be measured in flexion and extension to arrive at a measure of the disability of the hand as is often required for proper clinical evaluation and for the patient to obtain compensation for an injury which has limited his range of motion. At present, a therapist must sit with a patient and manually measure each individual angle of flexion and extension for each joint with a goniometer by isolating the joint, aligning it with the legs of the goniometer, and manually recording the measured included angle. Not only is this process tedious and time-consuming, and thus expensive to perform, but less time remains for the therapist to perform physical therapy with the patient. During the course of a patient's treatment, it is desirable to repeat these measurements over the time course of therapy to assess a patient's progress. Unfortunately, because there is some subjective element in the use of the goniometer and the current standard technique used in making hand function measurements, the repeatability of any particular examination is relatively poor. The variance of measurements from therapist to therapist has been so large with the standard goniometer so that the same therapist should measure the same patients each evaluation session. This is often not possible in a busy therapy center. This leads to uncertainty and ineffectiveness in assessing the patient's functional status and in designing treatment protocols.

Some attention has been paid in the prior art to the problem of evaluating and measuring the range of motion in the knee. Examples of these are found in U.S. Pat. Nos. 4,549,555 and 4,571,834. These references both contain the same disclosure relating to a knee laxity evaluator comprised of an instrumented seat, a restraint for restraining the thigh of the patient to the instrumented seat, a motion module consisting of a mechanical coupling extending between the seat and the patient's leg with a number of electromechanical rotary transducers for measuring the relative position of the leg, and a processor for analyzing the outputs of the seat and the motion modules to provide an indication of applied force and relative motion of the knee. The device disclosed is mechanically and operationally complex and is limited in its accuracy although it is probably adequate as measuring knee motion of a knee joint which is a very large joint whereas measuring finger motion requires much more delicate instrumentation.

Perhaps because of the bulky, mechanically complex construction of the device disclosed in these prior patents, the inventors herein are aware of a later commercial model of this device which is adapted for use with the spine which is comprised of a wand mounted at the end of a multi-jointed mechanical arm, the arm being adjustably mounted to a pole stand and having a rotary transducer at each of the joints of the arm. Apparently, a foot switch is also provided and the device is understood to be used by tracing an exterior outline corresponding to the perceived position of posterior elements and spinous processes in the spine with the wand as the foot switch is operated to input data corresponding to the shape of the spine to a computer which then performs an analysis including flexibilty and range of motion measurement. However, as with the prior art device disclosed in the patents mentioned above, the overall accuracy is limited by the use of the three rotary mono-angular (mono-articulated) single DOF transducers in the multi-jointed extension arm which are believed to generate only relative position data obtained by integrating a plurality of measurements over time, although the level of accuracy attainable is probably more than adequate for the measurement of the posterior elements of the dossal and lumbar spine.

The inventors herein are also aware of a prior art device consisting of a "data glove" as is described generally in U.S. Pat. No. 4,542,291 and also in a Scientific American magazine article appearing on the cover and within the Oct. 1987 issue. This device is essentially comprised of a glove which is slipped onto and encloses the hand and which contains a plurality of fiber-optic cables anchored at both ends to an interface board which run the length of each finger and doubles back. As the hand is measured, it is not visible to the operator. Each cable has a light-emitting diode at one end and a phototransistor at the other with the cables being treated so that light escapes when a finger flexes. Thus, a change in the amount of light received by the phototransistor, when converted into an electrical signal, is directly representative of a change in position or flexion of the finger such that the data glove can measure relative movement of the finger as it is flexed or extended. Additionally, an absolute position and orientation sensor is mounted near the wrist of the glove to provide a single absolute point of reference for the entire hand, although it does not provide data as to the position or angle of flexion or extension of any of the fingers themselves. The data glove provides simultaneous real time measurements concerning the relative motion or movement of the fingers but does not provide data corresponding to the absolute position of any of the fingers. Thus, to measure an angle of maximum flexion at each joint, the finger must first be placed in a known position and then the finger flexed to its position of maximum flexion as the output of the data glove is continuously monitored. The maximum angle of flexion may then be determined by comparing this known starting position with the angle of flexion computed by integrating continuously recorded measurements. Of course, there is some uncertainty in determining and repeating a known initial position and angle for a finger before it is flexed, especially if that finger is incapable of a full and complete range of motion. Once again, as with the prior art manual technique, and the rotary transducers of the prior art knee device, significant potential for error and subjectivity enter into the measurement of angles of flexion and extension with the data glove. There is no provision for competent human intervention in the operation of the data glove.

Still another problem in evaluating the hand is the complex nature of the wrist. Presently, in accepted standards of medical practice, the range of motion for the wrist is determined by having the patient grip a cylindrical object such as a pencil or the like, and holding the pencil in a vertical orientation which is defined as a neutral position. The patient is then told to rotate the pencil inwardly to its maximum extent and the angle is measured, and then to rotate the pencil outwardly to its maximum extent and that angle is measured as well. These angular measurements can then be used to determine the maximum pronation and supination. However, it is known that there is approximately 30 of additional total rotation contained in the joints between the radius and ulna and the fingers such that these measurements are not the true measurements of the range of motion of the wrist. Thus, there exists no protocol or methodology in the prior art to properly fully evaluate the true range of motion of the wrist. Furthermore, none of the prior art devices discussed above are capable of generating data which accurately provides the range of motion for the wrist. This is partially due to the fact that it is difficult to visualize the radius and ulna as the wrist is rotated, and for the further reason that the prior art systems have errors of measurement which are significant in measuring the small distances which through the wrist rotates.

To solve these and other problems in the prior art, the inventors herein have succeeded in designing and developing an upper extremity evaluation system which is disclosed and claimed in parent U.S. Pat. No. 4,922,925. This system is particularly adapted for and useful in measuring the range of flexion and extension of the joints of the hand, wrist and elbow and automatically calculating a degree of disability in accordance with American Medical Association (AMA) standards commonly used by the courts and workers compensation boards in determining the financial compensation due to a patient for an injury. That device adapts a three-dimensional spatial absolute position and orientation sensor into a computer measurement system which permits the convenient collection of data by a therapist corresponding to the absolute position of the proximal and distal segments at a joint in the fully extended as well as the fully flexed position. In other words, a therapist can quickly and conveniently enter data automatically into the computer which corresponds to the position of the various joints of the patient's hand as the hand is manipulated into one of only several different positions and held for only a brief period of time therein. Because absolute position data is measured and collected, much greater accuracy is attainable. Furthermore, because of the convenient methodology used to collect the data, an evaluation is also capable of a high level of repeatability. This has a dramatic impact on the accuracy of the initial assessment given to a patient, as well as the evaluation of treatment protocols through the course of the patient's rehabilitation. Still another advantage with that system is that for the first time accurate range of motion information can be easily collected by measuring the exact location of the radial and ulna styloid processes while the wrist is held in the neutral, supinated, and pronated positions. The computer may then eliminate the translation of these bones as they are moved from the computation to arrive at a true and accurate measure of the wrist's range of motion. Further information may also be obtained relating to the range of supination and pronation at the metacarpal level, which provide additional functional information of interest to the surgeon. However, perhaps the greatest advantage of the device is that it dramatically reduces the amount of therapists' time required to perform the clinical evaluation, and virtually eliminates the hand surgeon's time in evaluating the therapists' results. This is all achieved while significantly increasing the reliability and variability of the results.

In addition to measuring the angles of maximum flexion and extension, a dynamometer and pinch gauge are also connected directly to the computer for the direct entry of data corresponding to the grip strength and pinching strength of the hand and fingers. Still further data may be taken corresponding to other measurements, such as sensitivity, through the keyboard provided with the computer. Thus, the upper extremity evaluation system of the present invention permits a therapist to make an evaluation of any of the upper extremities, to input data gained through subjective manual measurements, and to permit such desired manipulation and calculation of the data to arrive at a degree of disability in accordance with AMA standards.

The protocol for entering data corresponding to the hand with the device disclosed in the parent patent is set forth in some detail therein. This protocol includes touching various parts of the patient's finger or hand with a wand or pointer, and pressing a foot switch when the wand or pointer is in the appropriate and desired location. This permits the therapist to choose the point in time for data entry to provide greater control over the evaluation. This process is repeated many times to completely digitize and measure a hand. One of the advantages offered by the protocol in the prior patented system is that the therapist maintains contact with the patient's hands as data are entered with the foot switch to thereby improve the data collection process. However, there are various points in the program which require the therapist to press a key on the keyboard, or a mouse, to move the program to another routine, change displays, or for various other reasons. Also, the therapist may initiate such computer actions upon his command which might be outside of or different from the usual and customary routine in collecting data while digitizing a hand. At these times, therapists ordinarily will release the wand or pointer and use their free hand to operate the keyboard or mouse. On some occasions, it may even be required that the therapist use both hands when it is required to depress multiple keys on the keyboard at the same time, or to speed data entry with the alphanumeric keys of the keyboard. On these occasions, the therapist looses contact with either the wand, or in some instances even the wand and the patient's hand, in order to facilitate entry of data into the computer.

In order to eliminate, or at least greatly minimize, those times when the therapist must release the wand and/or the patient's hand, the inventors herein have succeeded in enhancing the present system and utilizing a method to create a three-dimensional template, or desk top template, with a plurality of pre-defined areas, each of which perform a pre-determined function as a therapist places a wand within a pre-defined area and remains there for a pre-determined time period or activates a switch. In essence, the table top template may be reduced to virtually two dimensions to create a pseudo keyboard which when one of the keys is "digitized", the computer will recognize that input as requesting a particular subroutine to change displays, initiate data entry for other body locations, or otherwise substitute for data entry or computer command through depressing of a mouse or a pre-determined key on the keyboard. With the system operating in a desk top template mode, the therapist may readily maintain contact with the patient's hands as well as the wand or pointer which is highly desirable in ensuring accurate "digitizing" of a patient's hands. A therapist can ensure that the patient's hands remain in the same orientation during the measurement process and can also ensure that the data is properly entered into the computer, with the therapist having the correct prompts and displays before him to ensure proper data entry. This feature enhances use of the system and helps ensure even more reliable measurements.

Another improved feature of the hand digitizer system utilizes the three space digitizer/tracker in another operational mode. In addition to using the digitizer in a point mode, i.e. input of position data as the therapist depresses the foot switch, data may also be directly entered into the computer in this mode on a continuous mode and an incremental distance may be set to initiate data entry. For example, if the incremental distance is set at 0.5 inches, every time the wand or stylus is moved 0.5 inches, a position reading is taken. If the wand or stylus is not moved, then no reading is taken. In this continuous or "increment" mode, three dimensional contours of various parts of a patient's anatomy may be easily obtained. For example, tracing the wand or stylus over the surface of the hand will provide three dimensional data representative of the contour of the patient's hand which can then be further manipulated by the computer to calculate distances such as segment length as well as joint flexion. This "increment" mode is a three dimensional contour measurement which may also be used to map other body parts or make anthropometric measurements of body segment lengths, scar diameters, reach distances, and the like. These measurements can be of great importance to a therapist in order to measure a patient's progress in treatment and for developing additional treatment methods. As with the "increment" mode, the digitizer may also be used in a point mode with the foot switch in order to locate discrete or contiguous sets of points on a portion of the patient's anatomy for calculation of two or three dimensional distances, path length, or greatest dimension. These point measurements may also be used to determine body segment length, reach distance, scar diameter, and other such measurements of interest. These enhancements all contribute to making the hand digitizer a much more versatile clinical device.

A software package which operates on the control desktop personal microcomputer has been designed and developed by the inventors which guides and instructs the therapist as he/she proceeds through the evaluation process. This ensures a complete examination taken with the same methodology and helps improve the accuracy of results. In the prior art, significant inconsistencies of results are often noticed between therapists examining the same patient. With the present invention, these inconsistencies are thought to be significantly reduced. Furthermore, the software calculates angles of flexion and extension from the position data entered by the therapist, calculates the various anthropometric measurements, and makes further calculations in accordance with AMA standards to arrive at the degree of disability. A hand surgeon may then review these results and verify them in accordance with accepted medical practice. However, because of the increased reliability brought to the measurement and data entry portions of the evaluation, the amount of time and involvement of the hand surgeon can be significantly reduced thereby significantly reducing the cost of the evaluation to the patient while improving the results obtained thereby.

While the principal advantages and features of the present invention have been briefly described, a fuller understanding may be attained by referring to the drawings and description of the preferred embodiment which follow.

BRIEF DESCRIPTION OF THE DRAWINGS

FIG. 1 is a perspective view of a work station including the computer, printer, three-dimensional locator, and peripherals;

FIG. 2 is a top view of the work station of FIG. 1 with a patient and therapist depicted in a typical examination of an upper extremity (hand);

FIG. 3 is a side view of the work station of FIG. 1 detailing the mounting of the reference point for the three-dimensional point locator;

FIG. 4 is a side view of a finger with joints flexed into maximum flexion with points of measurement indicated thereon;

FIG. 5 is an example of a first template for therapists to use in collecting data;

FIG. 8 is a flow chart which enables a therapist to use the wand to trace contours and also make anthropometric measurements.

DETAILED DESCRIPTION OF THE PREFERRED EMBODIMENT

Figure 6:
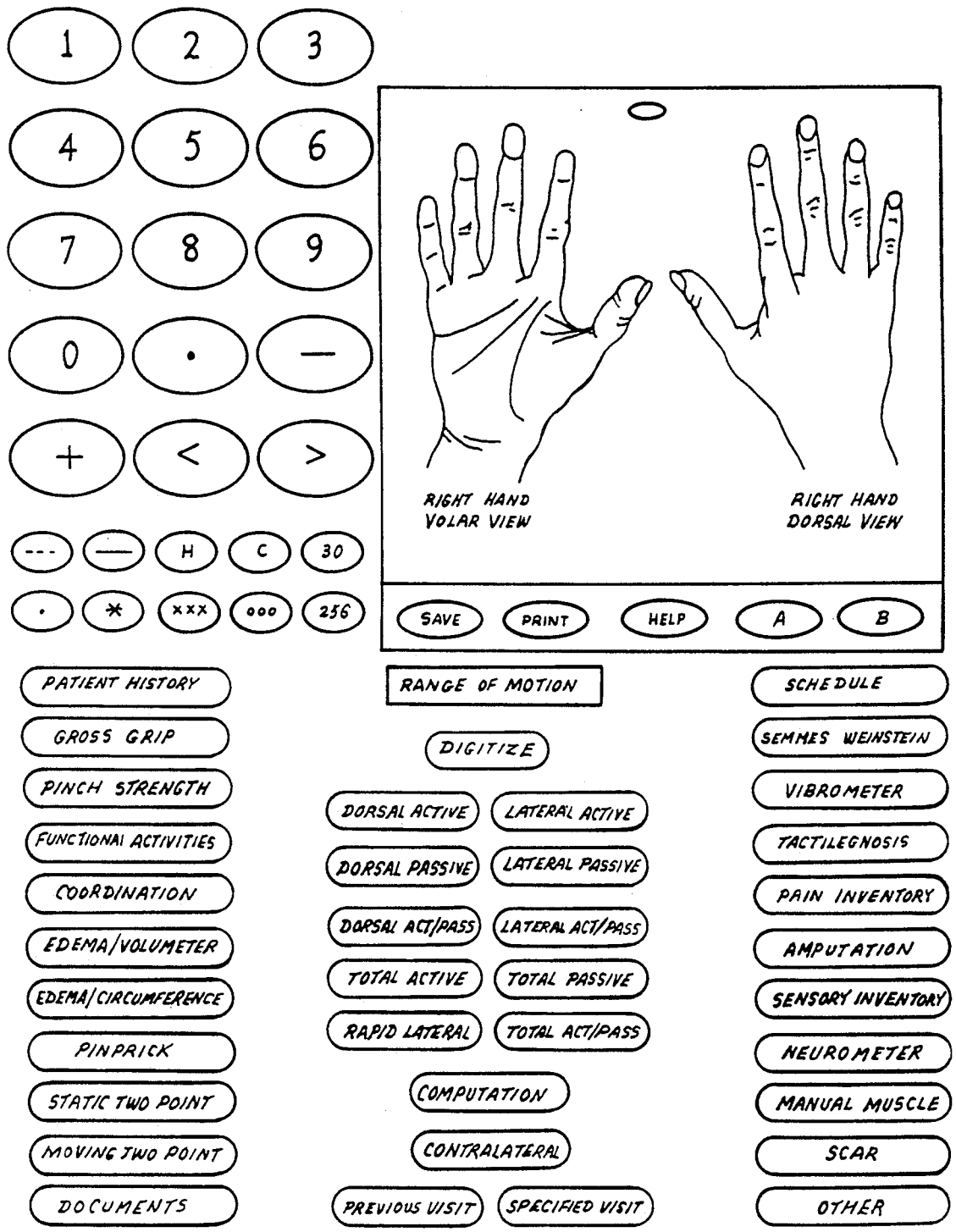
FIG. 6 is a second example of a similar template.

The upper extremity evaluation system 20 of the present invention can be conveniently mounted in a work station 22 wherein a small personal computer 24 such as a Macintosh SE computer (Apple Computer Corporation) with keyboard 26 and mouse may be installed. Additionally, a printer 28 or any other suitable peripheral output device may be utilized to permit automatic preparation of reports and the like as will be further explained herein. A three-dimensional position locator 30 may be interfaced to computer 24 and include a wand or pointer 32 along with a reference sensor 34 and foot switch 36 to permit a therapist to selectively input data to the computer 24 corresponding to the position of a point with respect to sensor 34. A three-dimensional position locator suitable for use herein is the 3SPACE tracker manufactured and sold by Polhemus Navigation Sciences Division of McDonnell Douglas Electronics Company, Colchester, Vt. Additionally, a grip dynamometer 38 and a pinch gauge 40 may be connected through an interface 42 directly to the computer 24. Examples of typical devices used by the inventors herein include a catalog number 1113 Jamar grip meter and pinch gauge and a MacAdious II SE expansion system interface. The analog signal of the grip meter is converted to a digital signal which is then fed into the computer database through the interface system. To improve the accuracy of the three-dimensional position locator 30, an aluminum panel 44 is mounted along the floor of the work station 22 such that it is thirty inches below the top surface of work station 22, with the reference sensor 34 being mounted five inches below the top surface of the work station 22. It has been found with this arrangement that an improved accuracy can be achieved with the particular components incorporated by the inventors in the best mode of their invention.

To more fully explain the operation of the invention, a sample scenario is contained in Exhibit A attached to the parent U.S. Pat. No. 4,922,925. This sample scenario describes the steps required to complete an examination of the upper extremities. The software program which controls the data input and calculation is described in a flow chart of Exhibit B attached to the parent U.S. Pat. No. 4,922,925. Although these exhibits are detailed explanations of the system, the system may be more briefly described for convenience as follows.

Essentially, the invention provides for the collection of position data of joints placed in flexion and extension which are then used by the computer to calculate angles of flexion and extension. Additionally, the computer provides for prompting of the therapist to enter other related data such as grip data, pinch strength data, sensitivity data, and other typical measurements as is known in the art. Data acquisition is achieved through the software program of Exhibit B. The database software used to create the reports is a standard database software, such as FileMakerPlus as is marketed by Forethought for the Apple Macintosh computer.

Joint range of motion information is collected in a process which combines the three-dimensional position locator and the computer. The therapist must first specify the portions of the upper extremities that will be analyzed, and then designate any joints that are either amputated or fused, the computer assuming that any non-designated joints are normal. The therapist is then prompted to supply the appropriate data through the usage of the present invention. That includes the process of touching the wand 32 to a point such as the MP apex 50 in FIG. 4 and then pressing foot switch 36 to cause entry of the data into the computer. This process is repeated at each of the points PIP apex 52, DIP apex 54, and fingernail 56. The three-dimensional position locator generates digital data corresponding to the relative position of those points 50-56 with respect to the reference sensor 34. From these several points taken about each of the fingers, angles of flexion and extension for those joints may be calculated by the computer. When done quickly by the therapist, there is virtually no tendency for the hands of the patient to be moved and hence the frame of reference is not altered or intended to be altered during the measurement process.

Figure 7:
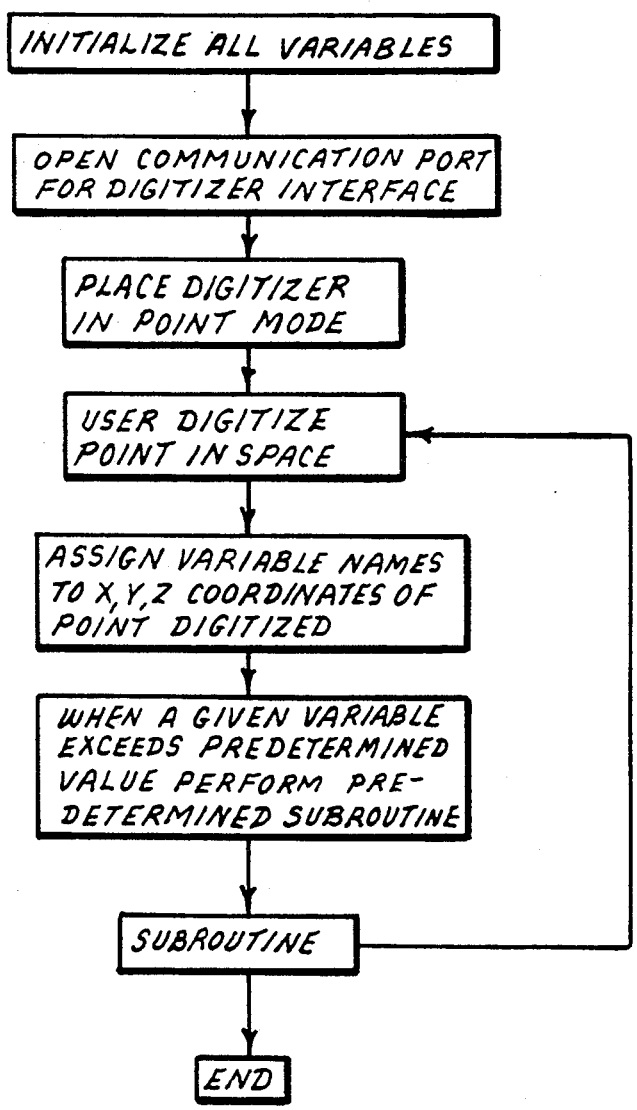
FIG. 7 is a flow chart for the program to permit a therapist to use the wand with the templates shown in FIGS. 5 and 6.

In order to facilitate the therapist's use of the wand 32 to greater advantage, the templates as shown in FIGS. 5 and 6 may be placed on a desk top or table top, and the program as shown by the flow chart of FIG. 7 used to provide an alternate therapist interface with the computer and to facilitate entry of the data in correct sequence. This eliminates the need for the therapist to drop the wand 32 and use his hand to make data entries or interact with the computer through the keyboard which would require a therapist to lose the close association between his hands and the patient's hands or other part of the patient's anatomy being measured at the time. In use, the wand 32 would merely be placed within the boundary of any of the buttons indicated by circles in the templates of FIGS. 5 and 6 and the foot switch depressed to indicate to the computer that the desired button was selected by the therapist. Upon entry of the position, the computer would recognize the correct variable and perform a set of instructions or commands corresponding thereto. With this protocol, the need for a therapist to interact with the computer's keyboard is virtually eliminated.

As shown in FIG. 8, an additional feature of the enhanced device disclosed herein includes the ability of the digitizer to trace a contour of a patient's body part with the digitizer being placed in the "increment" mode such that foot switch operation may be eliminated as the therapist traces the body part with the wand. This provides automatic data entry of a body contour, such as the outline of a patient's hand in the hand digitizer application. Additionally, this "increment" mode of operation may also be used to trace scars, body segment lengths, reach distances, and other anthropometric measurements as would be desired depending upon the particular application.

After the position information is used to calculate range of motion information, that data is stored in an associated logical record in the computerized database file which can then automatically generate reports In addition to usage of the wand or pointer 32, grip and pinch strength information can be input to the computer through use of the dynamometer 38 and pinch gauge 40. This digital data is stored in a file, similar to the range of motion data file, and is available to the database software to produce reports.

The therapist generally follows the instructions displayed on the screen of the computer to automatically enter range of motion data and grip and pinch strength data to any of the reports. There are three separate reports or forms. These include a data collection form, a final evaluation form, and a second version of the final evaluation form. Of course, any additional forms of any other desired nature may also be produced through simple reprogramming of the database as would be well known to one of ordinary skill in the art. These completed forms may then be printed out on the printer at the request of the therapist.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. In a computer based clinical evaluation device for measuring various physical parameters of a patient's anatomy, the device including means for a therapist to measure and input various physical locations of selected points with respect to a common reference with a pointer means, the improvement comprising means for defining a matrix in a space disassociated from a computer display, said matrix being comprised of a plurality of defined areas, each of said areas corresponding to a desired command or series of commands for said computer so that as said pointer means is positioned at one of said defined areas, said command or series of commands is performed by said computer.

2. In a computer based clinical evaluation device for measuring various physical parameters of a patient's anatomy, the device including means for a therapist to measure and input various physical locations of selected points with respect to a common reference with a pointer means, the improvement comprising means for automatically entering without operator intervention a continuous stream of position data into said computer corresponding to a continuous trace of a patient's body part as the pointer means is moved over the body part by the therapist.

3. The device of claim 2 wherein said patient's body part comprises a body segment.

4. The device of claim 2 wherein said patient's body part comprises a body scar.

5. The device of claim 2 wherein said patient's body part comprises a body hand.

6. The device of claim 2 further comprising means for selecting the distance between data points.

7. The device of claim 6 wherein said selection means includes means for selecting a single distance for separating each of said data points from its adjacent data points.

* * * * *